United States Patent [19]

Venturini

[11] Patent Number: 4,941,883
[45] Date of Patent: Jul. 17, 1990

[54] DISPOSABLE SAFETY SYRINGE

[76] Inventor: Aldo Venturini, Via Orbetello No. 176, 1-10148 Torino, Italy

[21] Appl. No.: 186,030

[22] Filed: Apr. 25, 1988

[30] Foreign Application Priority Data

Apr. 24, 1987 [IT] Italy ............................... 67343 A/87
Jul. 10, 1987 [IT] Italy ............................... 67600 A/87

[51] Int. Cl.$^5$ ............................................... A61M 5/18
[52] U.S. Cl. .................................... 604/186; 604/125; 604/183; 604/195
[58] Field of Search ............... 604/110, 192, 195, 196, 604/198, 183, 181, 186, 263, 125

[56] References Cited

U.S. PATENT DOCUMENTS

| | | | |
|---|---|---|---|
| 857,739 | 6/1907 | Kennerly et al. | 604/183 |
| 1,930,929 | 10/1933 | Eisenberg | 604/183 |
| 3,572,556 | 3/1971 | Pogacar | 604/186 |
| 3,978,846 | 9/1976 | Bailey | 604/125 |
| 4,284,077 | 8/1981 | Wagner | 604/186 |
| 4,747,830 | 5/1988 | Gloyer et al. | 604/110 |

Primary Examiner—Stephen C. Pellegrino
Assistant Examiner—Michael Rafa
Attorney, Agent, or Firm—McGlew & Tuttle

[57] ABSTRACT

Disclosed is a disposable safety syringe which comprises a reservoir and a tubular sheath. The reservoir serves to aspire therein or to inject therefrom a fluid, while the tubular sheath is integrally attached to and in fluid communication with the reservoir. In the sheath there is located a hollow needle and a needle-carrying means, suitably a bushing, which are axially slidable between a position of safety and protection for the needle within said sheath and an operative position in which the needle is fully protruding outside of the tubular sheath. When in this latter position, the needle is in air-tight fluid communication with the reservoir.

18 Claims, 6 Drawing Sheets

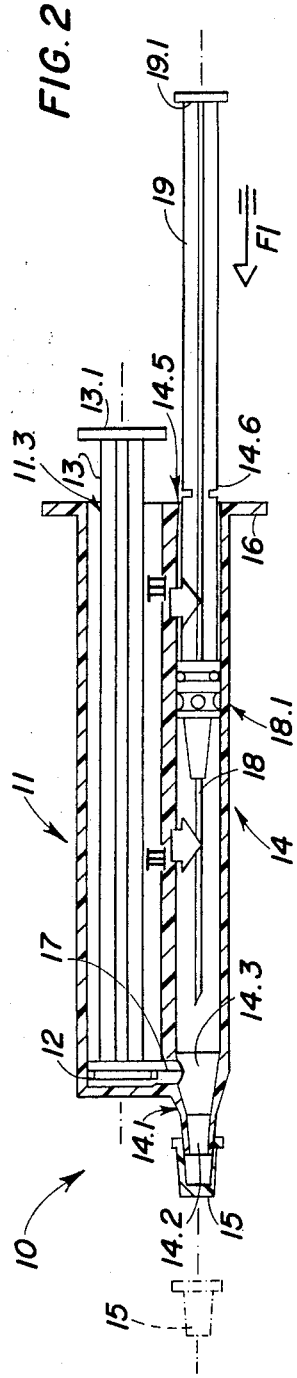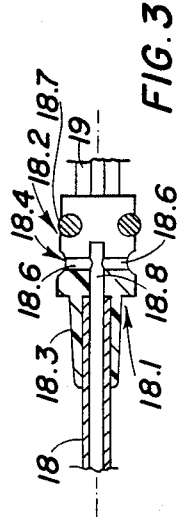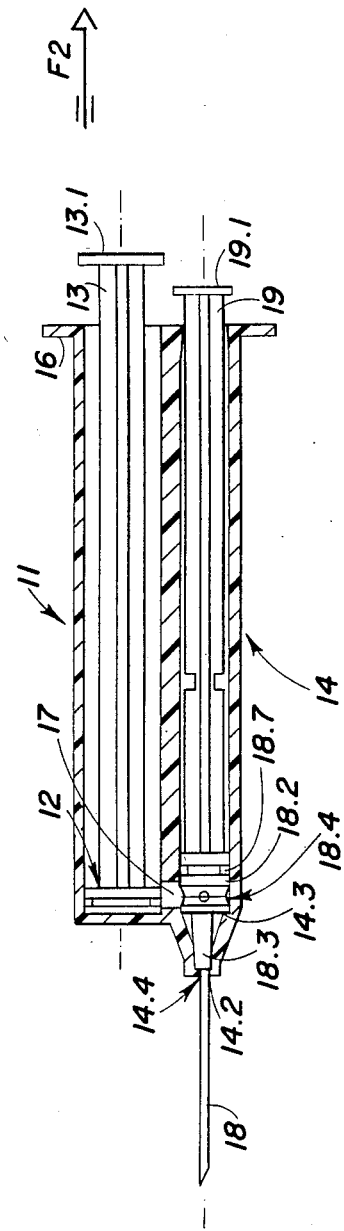

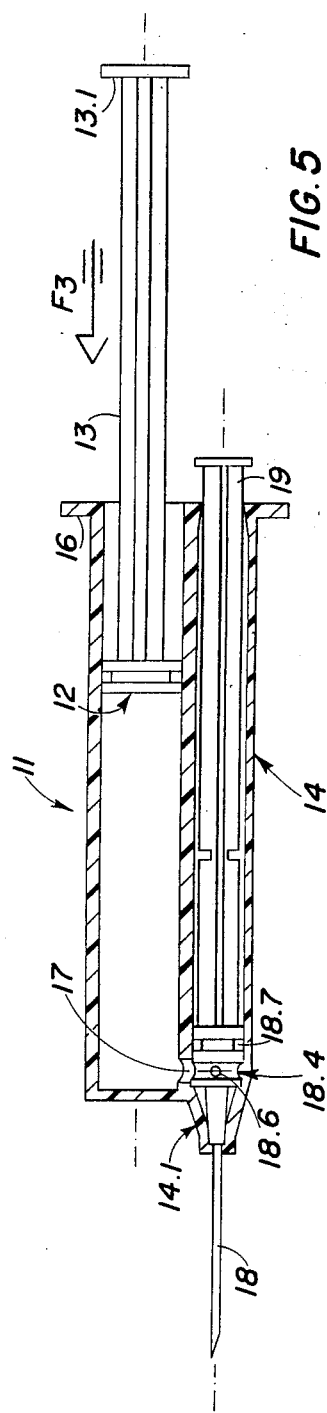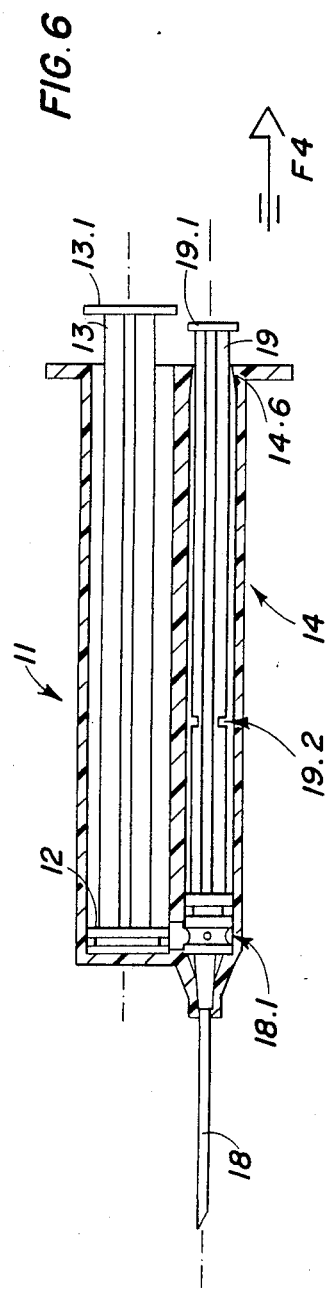

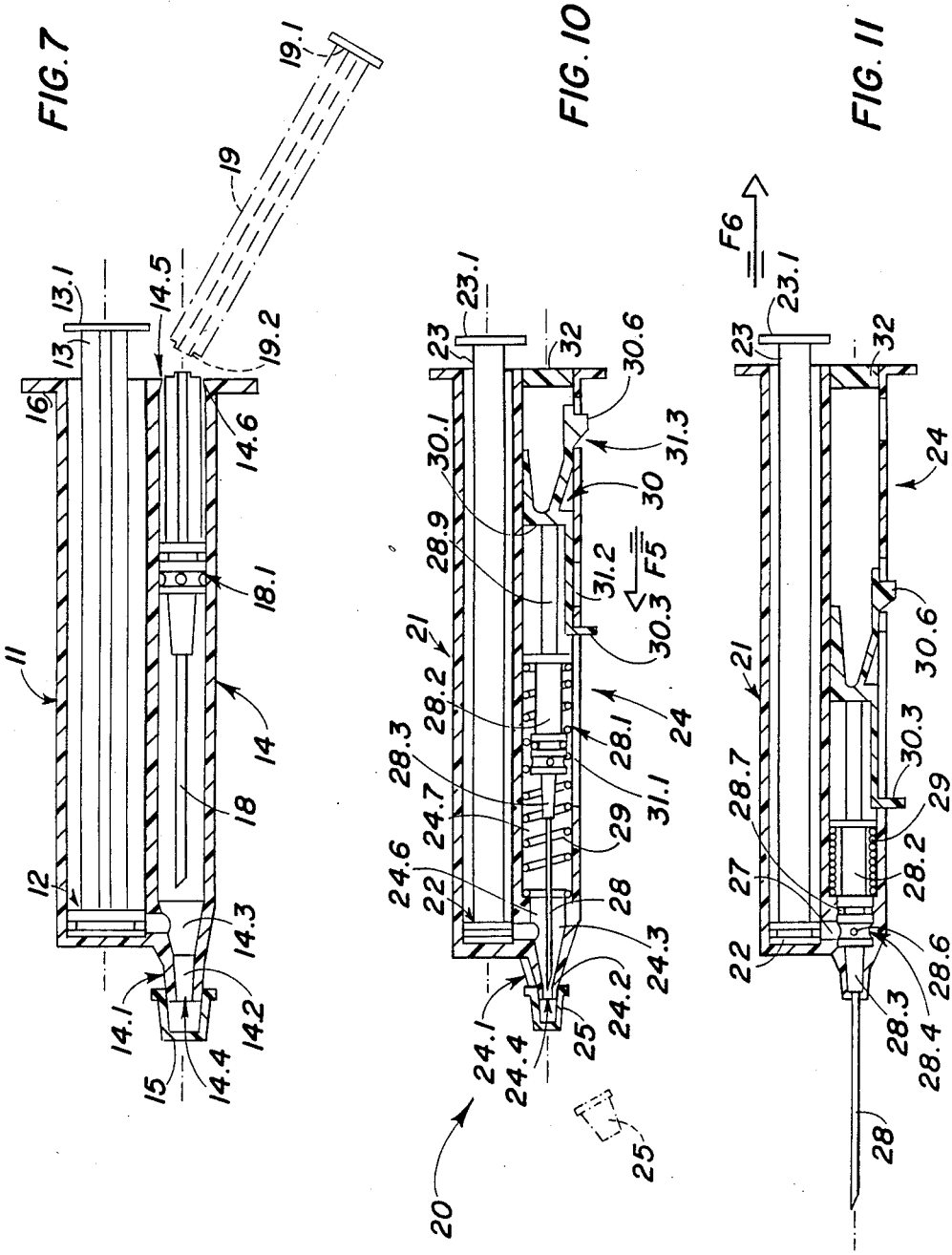

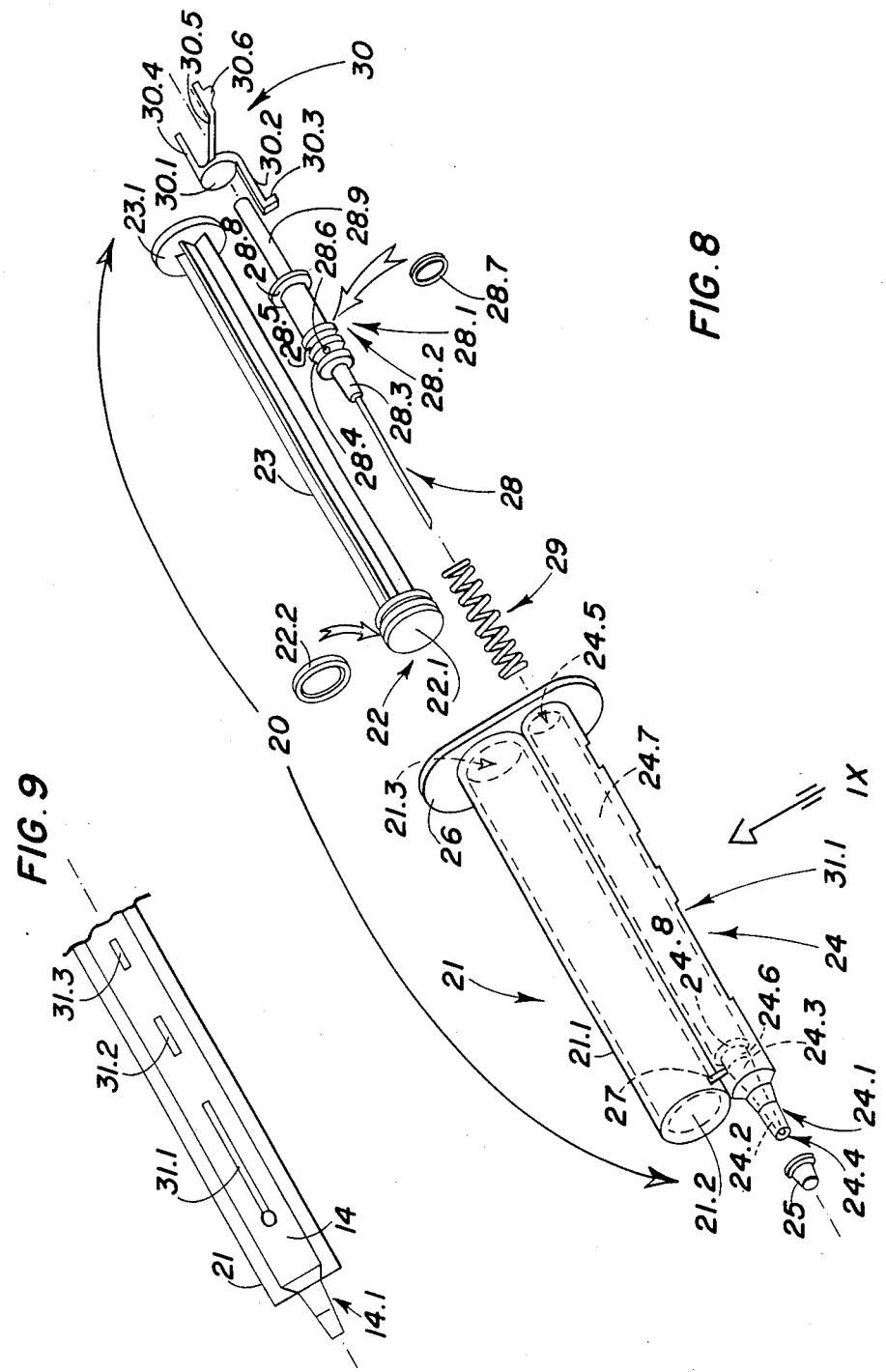

DISPOSABLE SAFETY SYRINGE

FIELD OF THE INVENTION

The present invention relates in general, to a construction for syringes an in particular to a new and useful disposable safety syringe.

BACKGROUND OF THE INVENTION

Disposable syringes are widely used, for instance, for injecting medications or for removing organic liquids for therapeutic or analytical medical purposes.

Such disposable syringes are commercially available sterilized and ready for use. They include a needle, protected within a removable, rigid and protective hood or sheath.

With such syringes, however, there exists the danger of involuntary removal of the sheath from its protective position before use of the syringe with consequent danger of needle contamination as well as of accidental injury to the personnel working with syringes.

An even greater danger of injury and infection exists in the subsequent disposal of the syringes after use. In fact, if the syringes are abandoned or discarded without their proper protective sheath, they constitute a means of possible injury and consequent eventual contamination or infection to those who, casually or inadvertently, might come into contact with such used syringes. On the other hand, the very act of replacing the sheath on the needle, after use, presents the danger of possible injury and, therefore, consequent possible contamination to the user.

In any event, the presence of the protruding needle in position of use from a disposable syringe constitutes a source of serious danger or infection to those who might come into contact with the syringe.

SUMMARY AND OBJECTS OF THE INVENTION

It is, therefore, the main object of the present invention to provide a disposable safety syringe capable of eliminating the disadvantages described hereinabove.

It is another object of the invention to provide a disposable safety syringe of which may be employed quickly in a simple manner and which is safe and reliable in operation.

Still another object of the invention is to provide a disposable safety syringe ready for use and provided, if desirable, with two needles for carrying out, for instance, first an operation of removal from a vial or from the human body of a given liquid by means of a first sterilized needle and, then, by means of the second sterilized needle the operation of injecting said given liquid.

Yet another object of the invention is to provide a disposable safety syringe which allows the injection or aspiration, for example, of liquids into or from cannulas, probes and the like without interference on the part of the needle, even when this is operatively positioned within the syringe.

The various features of novelty which characterize the invention are pointed out with particularity in the claims annexed to and forming a part of this disclosure. For a better understanding of the invention, its operating advantages and specific objects obtained by its uses, reference is made to the accompanying drawings and descriptive mater in which preferred embodiments of the invention are illustrated.

BRIEF DESCRIPTION OF THE DRAWINGS

FIG. 2 is a schematic, sectional and axial view of a syringe of the embodiment of FIG. 1, as presented for use;

FIG. 3 is a sectional and enlarged view taken along lines III—III of FIG. 2;

FIGS. 4 through 6 are schematic, sectional and axial views, illustrating respectively the syringe of the embodiment of FIGS. 1-3 in successive phases of operation, before the discarding of the syringe;

FIG. 7 is a schematic, sectional and axial view of the syringe of the embodiment of FIGS. 1-6, as it is discarded after use;

FIG. 8 is a perspective, exploded view of a second embodiment of the invention;

FIG. 9 is a partial, detailed view taken in the direction of arrow IX of FIG. 8;

FIG. 10 is a schematic, sectional and axial view of the syringe of the embodiment of FIG. 8 as presented for use;

FIGS. 11 through 13 are schematic, sectional and axial views illustrating respectively the syringe of the embodiment of FIGS. 8-10 in successive phases of operation, before the discarding of the syringe;

DESCRIPTION OF THE PREFERRED EMBODIMENTS

Figure 1:
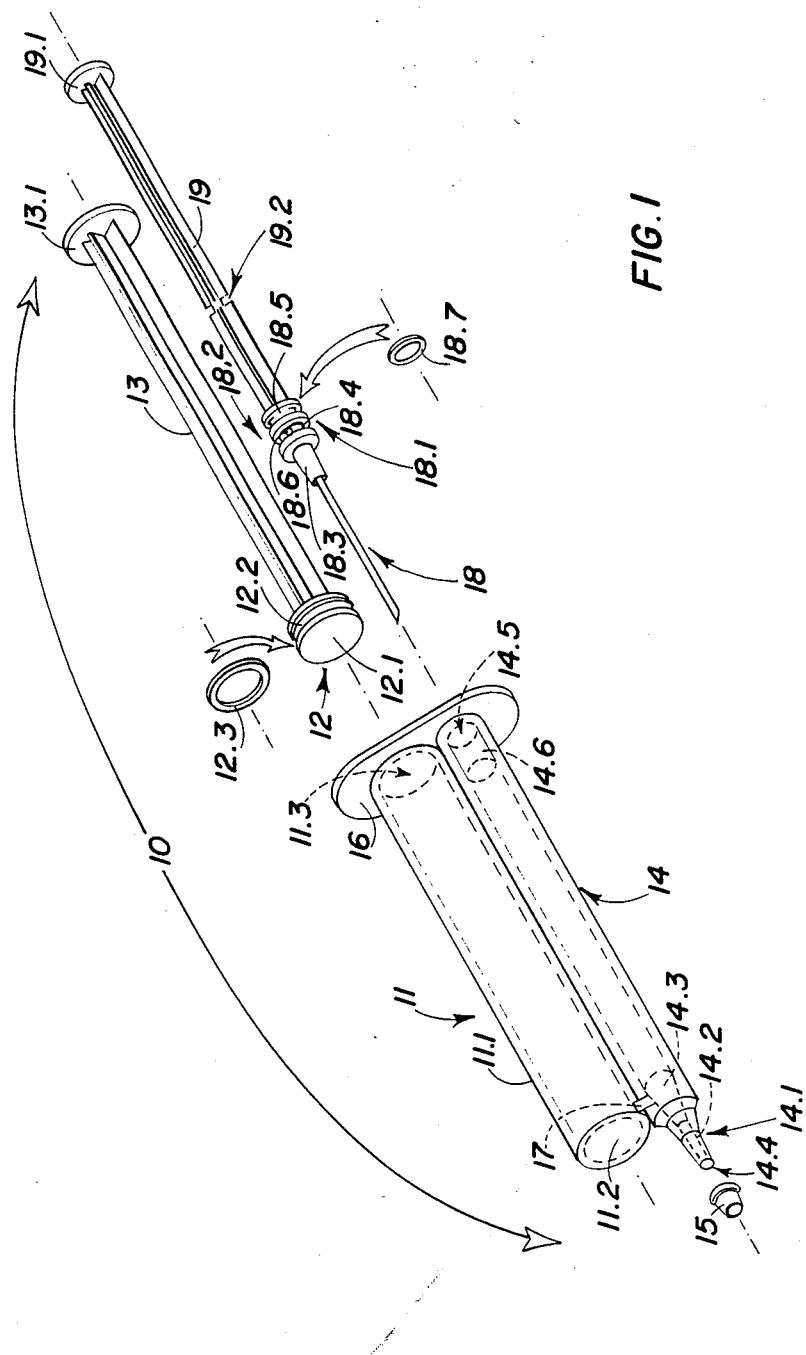
FIG. 1 is a perspective, exploded view of a first embodiment of the invention.
Figure 12:
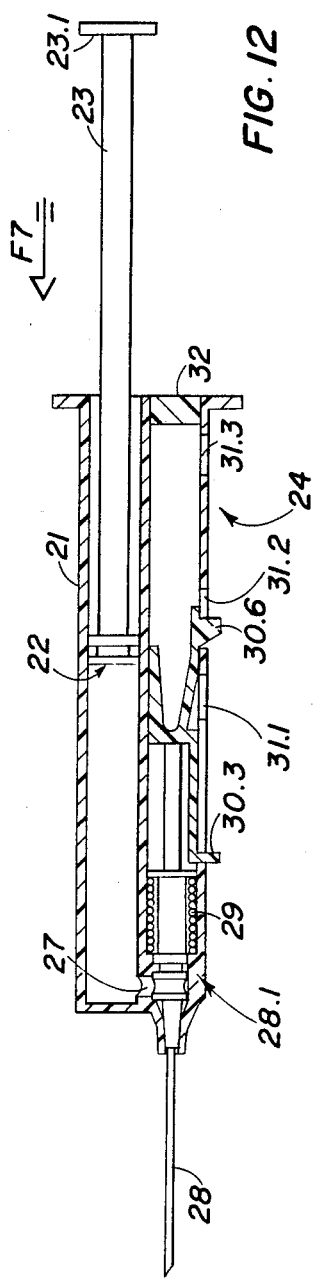
Figure 13:
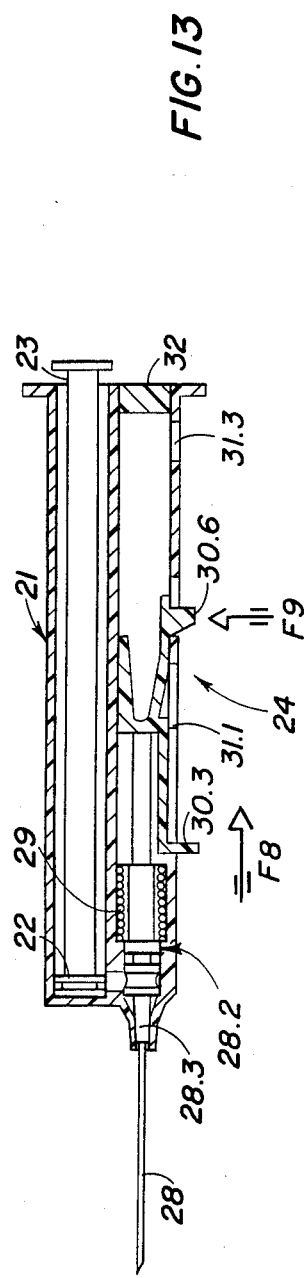
Figure 14:
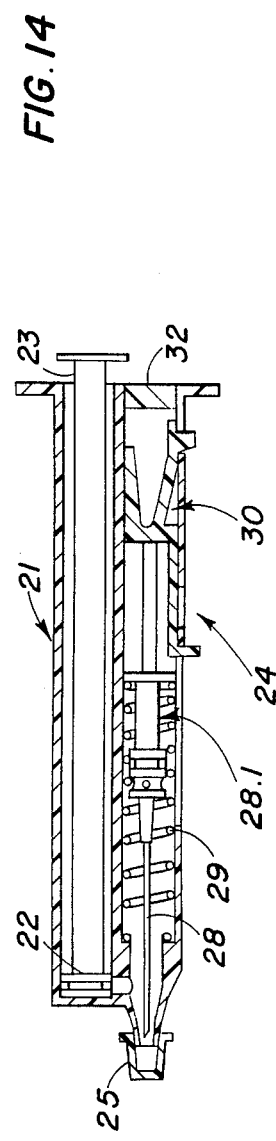
FIG. 14 is a schematic, sectional and axial view of the syringe according to FIGS. 8-13, as it is discarded after use.

Referring to the drawings, in particular the invention embodied therein in FIG. 1 includes a disposable safety syringe generally designated 10.

Syringe 10 includes a reservoir 11 for liquids to be sucked into or injected from it and consisting of a hollow cylinder 11.1 closed at one axial extremity thereof by a bottom wall 11.2. Reservoir 11 is, for instance; made of plastic material. In the reservoir 11 there is located, in a slidable and air-tight manner, a corresponding, discoid piston 12 with a flat head 12.1. Head 12.1 is provided with an annular, elastic sealing gasket 12.3 positioned in a circumferential throat 12.2 of its lateral surface. Gasket 12.3, suitably of rubber, insures the air-tight sliding along the inner cylindrical surface of reservoir 11. Piston 12 is integral with a rigid and coaxial stem 13 that has a cross-shaped cross-section. Stem 13 has a working base or foot 13.1 of a discoid shape formed and integral with its axial distal end from the piston 12 and extending externally of the reservoir 11 through an entrance or opening 11.3 of the reservoir 11. According to the illustrated example, piston 12, stem 13 and working foot 13.1 are made of a single piece, suitably of plastic material.

Syringe 10, further, has integral with the reservoir 11 a tubular, cylindrical sheath 14 with axis parallel to and substantially tangential to the hollow cylinder 11.1 of the reservoir 11. Sheath 14 has at one axial extremity thereof a conical beak 14.1 extending beyond the bottom wall 11.2 of the reservoir 11 and constituting the so-called tip of the syringe, for the separable coupling of a conventional syringe needle with a needle-carrying buckle (not shown). In correspondence with beak 14.1 in the tubular sheath 14, there is a coaxial frusto-conical seat 14.2 opening toward the interior of the sheath 14 into a flared aperture 14.3 of greater conical angle. Aperture 14.3 is also coaxial and is connected to the inner cylindrical surface of the sheath 14 in a rear position with respect to the bottom or base wall 11.2 of the reservoir 11. At the extremity opposed to the flared aperture 14.3, the frusto-conical seat 14.2 of the beak 14.1 opens into a coaxial hole 14.4 communicating with the outside. On the beak 14.1 there is usually placed a protective hood 15.

Sheath 14 has, further, in its axial extremity opposed to the beak 14.1 a mouth 14.5 substantially coplanar with the opening 11.3 of the reservoir 11. Mouth 14.5 opens toward the interior of the sheath 14 into a flared aperture 14.6 leading to the interior of the sheath to connect with the inner cylindrical surface thereof, following a conical configuration opposed to the configuration of the flared aperture 14.3 of the frusto-conical seat 14.2 of the beak 14.1.

In the axial extremity regions of the reservoir 11 and of the sheath 14, representing the respective apertures 11.3 and 14.5, there is provided a transverse wing 16 jutting out as an integral body from the outer peripheral surfaces of the reservoir and of the sheath like a flange forming a hilt or grip for the syringe 10.

A radial opening 17, constituting the intercommunicating air-tight passage between the reservoir 11 and the sheath 14, is provided in the wall section which is common to the reservoir and the sheath. Passage 17 is located rather near the bottom wall 11.2 of the reservoir 11—that is near the end of the run of piston 12 during injection in the reservoir 11—and opens into the flared aperture 14.3 of the frusto-conical seat 14.2 of the beak 14.1 of the sheath.

Syringe 10 comprises further a hollow needle 18 supported by a coaxial, partially hollow, slidable and water-tight bushing 18.1 positioned within the tubular cylindrical sheath 14. Needle 18 is, of course, coaxially oriented with respect to passage 14.4 of beak 14.1. Bushing 18.1 has a substantially cylindrical body 18.2, from which extends coaxially a frusto-conical head 18.3 which carries at its free extremity (of lesser diameter) needle 18. Cylindrical body 18.2 of the bushing has on its side surface a first circumferential throat 18.4, near the needle 18, and a second circumferential throat 18.5 distal from the needle. In correspondence with the first throat 18.4 there is in the bushing itself a pair of radial apertures 18.6 (see FIG. 3) diametrically opposed to each other and opening into the cavity of the bushing proper. In the second throat 18.5, instead, there is an elastic, annular, air-tight gasket 18.7, suitably formed of rubber, which insures the water-tight sliding action along the inner cylindrical surface of the tubular sheath 14. As clearly seen in FIG. 3, the inner cavity of bushing 18.1 is defined by an axial opening 18.8, developed within the frusto-conical head 18.3 of the bushing and constituting the seat for the mounting extremity of the needle 18, and forming an extension of the cavity of the needle proper, the axial opening 18.8 extends within the cylindrical body 18.2 of the bushing upright to the radial apertures 18.6 that open into the axial opening 18.1 itself.

At the axial extremity opposed to the frusto-conical head 18.3, the bushing 18.1 is attached to a rigid and coaxial stem 19 which has, according to the illustration given in the drawings, a cross-like cross-section. Stem 19 has a discoid working foot 19.1 at its free extremity, which extremity extends outside of the sheath 14 through aperture 14.5 thereof. Bushing 18.1, stem 19 and working foot 19.1 are made of a single piece, suitably of plastic material.

Stem 19 has a short portion of its length, intermediate its end, with a considerably reduced cross-section 19.2, so as to provide a zone of lesser strength adapted to be broken breakage, as it will be discussed later on.

The needle-carrying bushing 18.1, when mounted, is forced through aperture 14.5 into the sheath 14 to and beyond the flared aperture 14.6 of the sheath.

Referring now to FIGS. 8 through 14 the second embodiment of the invention includes (see FIGS. 8 and 10) a disposable safety syringe generally designated 20.

Similarly to syringe 10 of FIGS. 1-7, syringe 20 comprises a reservoir 21, formed of a hollow cylinder 21.1, closed at an axial extremity thereof by a bottom wall 21.2. In the reservoir 21 there is positioned a discoid, slidable and water-tight piston 22 with a flat head 22.1 and with an annular, elastic, water-tight gasket 22.2. Piston 22 is integral with a rigid, coaxial stem 23 having a discoid working foot 23.1, formed integrally with the axial extremity of the stem which is distal from the piston 22 and is extending outside of the reservoir 21 through an opening 21.3.

Further, syringe 20 has, in a body integral with the reservoir, a tubular cylindrical sheath 24 axially parallel to and substantially tangential to the hollow cylinder 21.1 of the reservoir 21. Sheath 24 has at an axial extremity thereof a conical beak 24.1, extending beyond the bottom wall 21.1 of the reservoir 21. In correspondence with the beak 24.1 and within the sheath 24 there is a coaxial, frusto-conical seat 24.2 that opens toward the interior of the sheath into a coaxial and flared aperture 24.3 of greater conical angle and connected to the inner cylindrical surface of the sheath 24 in a position somewhat in the rear with respect to the bottom wall 21.2 of the reservoir 21. At the extremity opposed to the flared opening 24.3, the frusto-conical seat 24.2 of the beak 24.1 opens up into a coaxial passage 24.4 which communicates with the outside. On the beak 24.1 there is generally a protective hood 25. Sheath 24, further, has in its axial extremity opposed to the beak 24.1 an aperture 24.5 substantially coplanar with respect to the opening 21.3 of the reservoir 11.

In the axial extremity of the reservoir 21 and of the sheath 24, where the respective openings 21.3 and 24.5 are, there is provided a transverse wing 26 shaped like a flange and forming the hilt or grip for the syringe 20.

A radial passage 27, forming a water-tight intercommunicating passage between the reservoir 21 and the sheath 24, is provided in the portion of wall that is common to the reservoir and the sheath. Passage 27 is positioned near the bottom wall 21.2 of the reservoir—that is corresponding to the end run of injection of piston 22—and opens into the flared aperture 24.3 of the frusto-conical seat 24.2 of the beak 24.1 of the sheath.

As a variant with respect to syringe 10, the cylindrical cavity of sheath 24 of syringe 20 has a cross-section which presents a smaller diameter in a short first portion 24.6 thereof starting from the flared aperture 24.3 of the seat 24.2, and a greater or larger diameter in a second portion 24.7 thereof extending from the bottom of the first portion 24.6 up to the opening 24.5 of the sheath proper. Between these two portions 24.6 and 24.7 of the cylindrical cavity of the sheath there is defined an annular shoulder 24.8.

Syringe 20 comprises, further, a hollow needle 28 supported by a coaxial, partially hollow, slidable and air-tight needle-carrying bushing 28.1 seated in the sheath 24, the needle 28 being coaxially oriented with respect to the passage 24.4 of beak 24.1. The bushing 28.1 has an intermediate body 28.2, substantially cylindrical, from which extends or protrudes coaxially a frusto-conical head 28.3 which carries at its free extremity of lesser diameter the needle 28. The intermediate body 28.2 of the bushing has on its side surface a first circumferential throat 28.4, near the needle 28, and a second circumferential throat 28.5, distal with respect to the needle. In correspondence with the first throat 28.4 there is in the bushing itself a pair of radial openings 28.6 (only one is visible in the drawings), which openings are diametrically opposed to each other and open into the cavity of the bushing proper. In the second throat 28.5, instead, there is an elastic, annular, air-tight gasket 28.7, suitably of rubber, for insuring the air-tight sliding along the inner cylindrical surface of the sheath in correspondence with the first portion 24.6 of lesser diameter. Similarly to the needle-carrying bushing 18.1 (FIG. 3), the inner cavity (not shown) of the bushing 28.2 of syringe 20 is defined by an axial hole developed in the frusto-conical head 28.3 of the bushing and constituting the mounting seat for the extremity of the needle 28 and forming an extension of the cavity of the needle proper. This axial hole or opening extends within the intermediate cylindrical body 28.2 of the bushing till it is in correspondence with the radial apertures 28.6 opening up into the axial hole itself.

At the extremity opposed to the frusto-conical head 28.3, the intermediate cylindrical body 28.2 has as a single unit a flange 28.8 of greater or larger diameter which engages slidably the surface of the portion 24.7 of the cylindrical cavity of the sheath. On one extremity of this flange 28.8, a helicoidal return spring 29 rests coaxially mounted on the needle-carrying bushing 28.1. The other extremity of the spring 29 is resting against the annular shoulder 24.8, formed in the cavity of the sheath 24. From the extremity of the spring which rests against the flange 28.8 a short stem 28.9 extends coaxially and also shaped as an integral part of the body 28.2.

In retro-position with respect to the bushing 28.1, in the portion 24.7 of larger diameter of the cylindrical cavity of the sheath 24, there is positioned a slidable skate 30 having a discoid head 30.1 and serving a sliding guide in the cavity. From the front of the head 30.1 a stem 30.2 extends in sliding contact with the surface of the cavity and from the side diametrically opposite to the reservoir 21, parallel to the stem 28.9 of the bushing 28.1. Stem 30.2 carries at its free extremity a tooth 30.3 radially extending toward the outside of the sheath 24 through a longitudinal guide slit 31.1 (see FIG. 9) formed in the sheath in a region diametrically opposed to the reservoir 21. Behind the discoid head 30.1 there protrudes a resting foot 30.4 positioned in sliding contact against the surface of the cylindrical cavity of the sheath, on the side of the reservoir. From the intermediate region of the rear surface of the discoid head 30.1, there extends a flexible lamella 30.5 directed toward the surface of the cylindrical cavity from the side opposed to the reservoir 21 and carrying at its free extremity an arresting wing 30.6 radially extending toward the interior of the sheath 24 alternately through one of the two longitudinal engaging slits 31.2 and 31.3 that are provided in the sheath 24 (see FIG. 9). These two slits have different lengths, slit 31.2 extending farther than slit 31.3, and the two slits are aligned with respect to each other and with respect to the guide slit 31.1. The arresting wing 30.6 presents one face toward the beak 24.1 of the sheath and is shaped like a slide, so as to facilitate its disengagement from the respective engaging slit in the advance of the skate 30 toward the beak 24.1. The other (opposed) face of the wing is substantially normal to the axis of the sheath, so as to insure the arresting action of the wing with respect to the skate 30, contrary to the elastic pushing action of the return spring 29.

The free extremity of the stem 28.9 of the needle-carrying bushing 28.1 is resting against the frontal surface of the discoid head 30.1 of the skate 30 Skate 30 may be made, for example, of a single plastic piece.

The aperture 24.5 of the tubular sheath 24 is closed by means of a stopper 32 (see FIGS. 10-14).

OPERATION OF SYRINGE 10 ACCORDING TO THE INVENTION (FIGS. 2-7):

Syringe 10 is ready for use, as illustrated in FIG. 2, that is with the needle retracted in the position of safety inside the sheath 14 and with the protective hood mounted on the beak 14.1. To use the syringe the hood 15 is removed, the syringe is gripped by means of the wing 16 and a pushing action is exerted on the woking foot 19.1 of stem 19, in the axial direction (arrow F1 in FIG. 2), bringing the needle 18 out through the aperture 14.4 of the beak or tip 14.1, and causing the bushing 18.1 to engage the flared opening 14.3 of the frusto-conical seat 14.2 of the beak. Continuing the axial pushing action, the head 18.3 and the cylindrical body 18.2 of the bushing are forced into their respective conical seats 14.2 and 14.3 of the beak and of the sheath, respectively. There is attained, thusly, a stable and operative positioning of the needle 18, fully extracted from the sheath 14, as well as the formation of an air-tight region in the sheath between the head 18.3 (engaged in the conical seat) and the annular air-tight gasket 18.7 of the bushing 18.1 (see FIG. 4). The annular and air-tight region in the sheath 14 is in air-tight communication with the reservoir 11 by means of the passage 17, while in such a position of the bushing, the circumferential throat 18.4—on which open the radial holes 18.6—is placed in correspondence with the said hole 17. The piston 12 is then acted upon, by means of the stem 13, so as to obtain a suction within the reservoir 11 (arrow F2, FIG. 4), through the cavity in the needle 18, the axial opening 18.8, the radial holes 18.6 of the bushing, the annulat air-tight region of the sheath and the intercommunicating passage 17. Similarly, by an inverse operation, the injection of a liquid is obtained starting from the reservoir 11 (see arrow F3, FIG. 5). Executed the injection, the needle 18 is retracted to the safety position within the sheath 14 by exerting an axially sliding action on the stem 19 (see arrow F4, FIG. 6) until the stem 19 is positioned with its weak area 19.2 outside of the opening 14.5 of the sheath. The stem is then broken (see FIG. 7), confining the needle 18 within the sheath. The hood 15 is then reattached on the beak 14.1 and the syringe may then be safely discarded. It is to be observed that the retro extraction of the bushing 18.1 with needle 18 from the flared aperture 14.6 is prevented, because the bushing proper would be forced to be engaged in this flared aperture.

Although not illustrated, it is clear that the aspiration operation of a fluid may be executed by attaching a conventional needle on the beak 14.1, after removal of the hood 15, thus avoiding the contamination of the needle 18 retracted in the sheath 14. After removal of the conventional needle, needle 18 may be extracted and the above operation may be carried out.

Further, syringe 10 with needle 18 retracted in the sheath, may be employed for injecting or aspiring fluids into or from cannulas, probes and the like, without interference on the part of the needle itself.

With needle retracted, syringe 10 is ready for use also in laboratory operations, like a pipette for withdrawals and the like.

OPERATION OF SYRINGE 20 ACCORDING TO THE INVENTION (FIGS. 10-14):

Syringe 20 is ready for use as illustrated in FIG. 10. After removal of the hood 25, a pushing action is exerted on the skate 30 by means of its tooth 30.3 protruding from the guide slit 31.1 (see arrow F5, FIG. 10). Arresting wing 30.6 is, thus, caused to disengage from the engaging slit 31.3 through the elastic bending of the lamella 30.5 which carries it. The wing, thus, engages by snapping action the other engaging slit 31.2, wherein the arresting wing 30.6 can effect a partial run, corresponding to the run of the tooth 30.3 in the respective guide slit 31.1. This run determines the forced engagement of the frusto-conical head 28.3 and of the intermediate cylindrical body 28.2 of the needle-carrying bushing 28.1 in their respective conical seats 24.2 and 24.3 of the beak 24.1 and of the sheath 24, with resultant full extraction of the needle 28 through the passage 24.4 (see FIG. 11). The air-tight gasket 28.7 insures in such a position a sealing action with respect to the wall of the area or region 24.6 of the cavity of the sheath, while the annular throat 28.4—into which the radial apertures 28.6 are opening—of the bushing 28.1 is positioned in correspondence with the intercommunicating passage 27 between the sheath and the reservoir.

Thus, a stable operative positioning of the needle 28 is obtained, as well as the air-tight communication of the cavity of of the needle with the reservoir 21, in a manner fully analogous to the above description referring to syringe 10. The return spring 29 is, thusly, elastically loaded. The air-tight aspiration operation (see arrow F6, FIG. 11) and the air-tight injection operation (see arrow F7, FIG. 12) are effected in a conventional manner by sliding the piston 22 within the reservoir 21. Finally, to retract the needle in the position of safety and protection within the tubular sheath, the needle-carrying bushing 28.1 is disengaged from its forced coupling or attachment to the respective conical seats 24.2 and 24.3 of the beak 24.1 and of the sheath 24 by acting manually on the tooth 30.3 in the direction indicated by the arrow F8 in FIG. 13. This manual operation is required for purpose of safety against an involuntary return of the needle 28. As a result of such a retraction, the arresting wing 30.6 engages the bottom transversal surface of the slit 31.2. It is, therefore, sufficient to reenter under pressure the arresting wing within the sheath 24, overcoming with a manual push (see arrow F9, FIG. 13) the elastic action of the lamella 30.5 which carries it. This results in an elastic action on the part of the return spring 29, which determines the automatic return of the needle 28 to the position of safety and protection within the sheath 24, as well as the return of the arresting wing to the engaging slit 31.3. The protective hood 25 is, then, replaced and the syringe 20 may be discarded with the utmost safety.

Obviously, numerous variants may be effected, in practice, with respect to the device as described and illustrated hereabove. Thus, for instance, the reservoir may be of the type suitable for containing the so-called vacutainer, a vacuum container, or it may be of the type with an elastic membrane; concurrently, the sheath and the needle-carrying means may be conformed in a manner to insure the functions of sliding guide and of stable, operative and air-tight positioning of the needle within the sheath.

Further, the intercommunication between the cavity of the needle and the reservoir may be effected, via the sheath, with the needle as intermediary. For instance, the needle may be provided with radial openings in its wall and with suitable sealing means. In this case, the sheath will be shaped in such a manner as to receive in air-tight condition the needle and to engage forcedly and air-tightly the needle-carrying means, serving as support for the needle.

While specific embodiments of the invention have been shown and described in detail to illustrate the application of the principles of the invention, it will be understood that the invention may be embodied otherwise without departing from such principles.

What is claimed is:

1. A disposable safety syringe comprising:
an elongated cylindrical reservoir for fluids to be aspired therein or injected therefrom; a plunger housed in said cylindrical reservoir in sealing engagement with said reservoir for axial sliding therein for sucking liquids into said reservoir and ejecting liquids from said reservoir; a tubular sheath positioned adjacent said reservoir in side to side relationship with said reservoir; a fluid communication passage formed between said reservoir and said tubular sheath; a hollow needle positioned within said tubular sheath; needle support means for supporting said hollow needle for sliding movement between a first position of safety in which said needle is fully within said sheath and a second position of operation in which said needle protrudes from said sheath; and, communication and sealing means connected to said needle support means for providing fluid communication between a hollow portion of said needle and said fluid communication passage in a sealed air-tight manner for allowing fluid to communicate from said reservoir to said hollow portion of said needle.

2. A disposable safety syringe according to claim 1, further comprising: a seat portion provided at an axial extremity of said sheath, said sealing and communication means including sealing and centering means for sealing and centering said needle with respect to said seat portion and for forming an air-tight chamber in said tubular sheath for achieving air-tight fluid communication between said hollow portion of said needle and said reservoir.

3. A disposable safety syringe according to claim 2, wherein: said seat portion of said tubular sheath opens toward an interior of said sheath into an aperture which is coupled to said sealing and communication means in an air-tight manner.

4. A disposable safety syringe according to claim 1, wherein: said sealing and communication means includes sliding sealing means for air-tight sliding along the entire axial cavity of said tubular sheath such that fluid may be aspired or injected when said needle is in said safety position.

5. A disposable safety syringe according to claim 1, wherein: said sealing communication means is formed integral with stem that extends externally of said sheath.

6. A disposable safety syringe according to claim 5, wherein: said stem is formed with a breakable portion which is located externally of said sheath when said needle is in said safety position.

7. A disposal safety syringe according to claim 1, further comprising: a sliding skate connected to said sealing and communication means; a flange connected to said sealing and communication means adjacent said sliding skate and a spring positioned between an end of said sheath and said flange portion to bias said needle into said safety position, said sliding skate having means for fixing said sealing and communication means in said operative position against the force of said spring.

8. A disposable safety syringe according to claim 1, wherein: said tubular sheath includes a needle end with a beak portion, said beak portion including means for connecting said beak portion with needle carrying means of a conventional needle.

9. A disposable safety syringe according to claim 1, wherein: said tubular sheath includes an end opposed to said needle having an internally flared aperture opening toward the interior of said sheath, said flared aperture including means for engaging said sealing and communication means to prevent removal of said sealing and communication means.

10. A disposable safety syringe according to claim 1, further comprising: a piston connected to an actuating stem positioned within said reservoir, said piston being in slidable air-tight engagement with an interior portion of said reservoir.

11. A disposable safety syringe according to claim 1, wherein: said reservoir is a chamber formed of an elastic membrane.

12. A disposable safety syringe comprising: an elongated cylindrical reservoir member; an elongated cylindrical sheath formed adjacent said reservoir, said reservoir being connected to said sheath in side to side arrangement, each of said reservoir and sheath having a needle end and a manipulation end, the interior of said reservoir being in fluid communication with the interior of said sheath adjacent said needle end; a a hollow needle adapted to be positioned within said sheath and to extend out of a needle hole formed in said needle end of said sheath, said needle having a hollow portion formed therein; a needle support member for supporting said needle, said needle support member being adapted to be positioned in an active position in which said needle protrudes from said sheath through said needle hole and a safety position in which said needle is maintained within said sheath; sealing and communication means associated with said needle support member, for providing communication between said hollow portion of said needle and said reservoir when said needle support member is in the active position and to form an air-tight seal for air-tight fluid communication when said needle is in an active position and to form an air-tight seal when said needle is in an inactive position.

13. A disposable safety syringe according to claim 12, wherein: said sheath includes a conical tip at said needle end surrounding said needle hole; said needle support member including a conical sealing portion adapted to engage an interior of said conical tip for sealing said needle hole when said needle is in an active position.

14. A disposable safety syringe according to claim 12, wherein: said needle end of said sheath includes an interior flange adjacent said needle end; said needle support member including a flange spaced from said sealing and communicating means and movable with said needle support member; a spring positionable between said sheath flange and said needle support member flange to urge said needle support into said safety position; means for maintaining said needle support member in said active position against a biasing force of said spring; and, manipulation means connected to said needle support member for positioning said needle in said fixed active position and for removing said needle from said active position into said safety position.

15. A disposable safety syringe, comprising: an elongated cylindrical reservoir member, in which a plunger is housed in tight and axially sliding fashion for sucking liquids into and injecting liquids from said reservoir; an elongated tubular sheath formed adjacent said reservoir in side to side arrangement and in fluid communication with said reservoir, each of said reservoir and sheath having a manipulation end and said sheath having a needle end; a hollow needle positioned within said sheath and a needle support member provided within said sheath for sliding movement between an active position of the needle, in which said needle protrudes from said sheath through an needle hole formed in said needle end of said sheath, and a safety position of the needle, in which said needle is withdrawn and maintained within said sheath; communication and sealing means connected to said needle support for providing communication between the hollow needle and the reservoir when said needle is in the active position and to form an air tight seal for air tight fluid communication between the hollow needle and the reservoir when said needle is in the active position, and to form an air tight seal when said needle is withdrawn in the safety position within said sheath.

16. A disposable safety syringe according to claim 12 wherein said communication and sealing means comprises a first throat (18.4) of the needle support (18.1), near the needle (18), apertures (18.6) opening into said first throat and cavity (18.8) of the needle support forming an extension of the cavity of the hollow needle, and an annular, air tight gasket (18.7) fitted in a second throat (18.5) of the needle support, distal from the needle.

17. A disposable safety syringe according to claim 15, characterized in that it comprises a stem (19) formed integral with said needle support (18.1) and that extends externally of said sheath for manually causing said hollow needle to slide within said sheath between said active position and said safety position.

18. A disposable safety syringe according to claim 15, characterized in that it comprises, within said sheath (24), a sliding skate (30) connected to said needle support (28.1), a flange (28.8) formed integral with said needle support, and a spring (29) positioned between an axial end of said sheath and said flange to bias said needle support together with the needle into said safety position, said sliding skate (30) being provided with arresting means (30.6) which engages a slit (31.2) in the sheath when said skate is manually pushed towards said needle end of the sheath, to fix, disengageably, said needle support in said active position of the needle against the force of said spring.

* * * * *

UNITED STATES PATENT AND TRADEMARK OFFICE
CERTIFICATE OF CORRECTION

PATENT NO. : 4,941,883
DATED : July 17, 1990
INVENTOR(S) : Venturini

It is certified that error appears in the above-identified patent and that said Letters Patent is hereby corrected as shown below:

Please correct Claim 12 of the Patent to read as follows:

12. A disposable safety syringe comprising: an elongated cylindrical reservoir member; an elongated cylindrical sheath formed adjacent said reservoir, said reservoir being connected to said sheath in side to side arrangement, each of said reservoir and sheath having a needle end and a manipulation end, the interior of said reservoir being in fluid communication with the interior of said sheath adjacent said needle end; a hollow needle positioned within said sheath and extending out of a needle hole formed in said needle end of said sheath, said needle having a hollow portion formed therein; a needle support member for supporting said needle, said needle support member being positioned in an active position in which said needle protrudes from said sheath through said needle hole and being positioned in a safety position in which said needle is maintained within said sheath; sealing and communication means associated with said needle support member, for providing communication between said hollow portion of said needle and said reservoir when said needle support member is in the active position and to form an air-tight seal for air-tight fluid communication when said needle is in an active position.

UNITED STATES PATENT AND TRADEMARK OFFICE
CERTIFICATE OF CORRECTION

PATENT NO. : 4,941,883
DATED : July 17, 1990
INVENTOR(S) : Venturini

It is certified that error appears in the above-identified patent and that said Letters Patent is hereby corrected as shown below:

Please correct Claim 13 of the Patent to read as follows:

13. A disposable safety syringe according to claim 12, wherein: said sheath includes a conical tip at said needle end surrounding said needle hole; said needle support member including a conical sealing portion engaging an interior of said conical tip for sealing said needle hole when said needle is in an active position.

Please correct claim 14 of the Patent to read as follows:

14. A disposable safety syringe according to claim 12, wherein: said needle end of said sheath includes an interior flange adjacent said needle end; said needle support member including a flange spaced from said sealing and communication means and connected with said needle support member; a spring positioned between said sheath

UNITED STATES PATENT AND TRADEMARK OFFICE
CERTIFICATE OF CORRECTION

PATENT NO. : 4,941,883
DATED : July 17, 1990
INVENTOR(S) : Venturini It is certified that error appears in the above-identified patent and that said Letters Patent is hereby corrected as shown below:

flange and said needle support member flange to urge said needle support into said safety position; means for maintaining said needle support member in said active position against a biasing force of said spring; and, manipulation means connected to said needle support member for positioning said needle in said fixed active position and for removing said needle from said active position into said safety position.

Signed and Sealed this

Fourteenth Day of May, 1996

Attest:

BRUCE LEHMAN

*Attesting Officer*   *Commissioner of Patents and Trademarks*